United States Patent
Inagaki et al.

(10) Patent No.: US 12,161,154 B2
(45) Date of Patent: Dec. 10, 2024

(54) AEROSOL SUPPLY DEVICE

(71) Applicant: Japan Tobacco Inc., Tokyo (JP)

(72) Inventors: Michihiro Inagaki, Tokyo (JP); Yuki Abe, Tokyo (JP); Miki Wakamatsu, Tokyo (JP); Tatsuya Suganuma, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 555 days.

(21) Appl. No.: 17/495,434

(22) Filed: Oct. 6, 2021

(65) Prior Publication Data
US 2022/0022534 A1    Jan. 27, 2022

Related U.S. Application Data

(63) Continuation of application No. PCT/JP2020/014316, filed on Mar. 27, 2020.

(30) Foreign Application Priority Data

Apr. 9, 2019   (JP) .................... 2019-074362

(51) Int. Cl.
*A24F 40/10* (2020.01)
*A24F 40/05* (2020.01)
*A24F 40/51* (2020.01)
*B05B 17/06* (2006.01)

(52) U.S. Cl.
CPC .............. *A24F 40/05* (2020.01); *A24F 40/10* (2020.01); *A24F 40/51* (2020.01); *B05B 17/0653* (2013.01)

(58) Field of Classification Search
None
See application file for complete search history.

(56) References Cited

U.S. PATENT DOCUMENTS

| | | | |
|---|---|---|---|
| 10,671,031 B2 * | 6/2020 | Hawes | ................... G05B 15/02 |
| 2009/0133691 A1 | 5/2009 | Yamada et al. | |
| 2013/0327322 A1 | 12/2013 | Bentvelsen et al. | |
| 2017/0108840 A1 | 4/2017 | Hawes et al. | |
| 2017/0156397 A1 | 6/2017 | Sur et al. | |

(Continued)

FOREIGN PATENT DOCUMENTS

| CN | 108937059 A | 12/2018 |
|---|---|---|
| CN | 108969853 A | 12/2018 |

(Continued)

OTHER PUBLICATIONS

International Search Report (PCT/ISA/210) issued in PCT/JP2020/014316, mailed on Jun. 16, 2020.

(Continued)

*Primary Examiner* — Felix O Figueroa
(74) *Attorney, Agent, or Firm* — Birch, Stewart, Kolasch & Birch, LLP (57) ABSTRACT

This aerosol supply device is provided with: an accommodating section (cartridge) that accommodates a liquid; an atomizing unit that atomizes the liquid to generate an aerosol; and an atomizing amount adjusting unit (gyro sensor and control unit) that adjusts the atomizing amount of the atomizing unit. The aerosol supply device is characterized in that the atomizing amount adjusting unit (gyro sensor and control unit) stabilizes the atomizing amount regardless of the inclination of the aerosol supply device within at least a certain range.

7 Claims, 6 Drawing Sheets

(56) References Cited

U.S. PATENT DOCUMENTS

2017/0280771 A1 10/2017 Courbat et al.
2018/0339303 A1 11/2018 Inoue et al.
2022/0022546 A1* 1/2022 Inagaki .................. A24F 40/53
2022/0022551 A1* 1/2022 Inagaki ............... A61M 15/002

FOREIGN PATENT DOCUMENTS

| CN | 113229531 A * | 8/2021 |
| EP | 2 875 740 A2 | 5/2015 |
| JP | 2-187165 A | 7/1990 |
| JP | 4-236962 A | 8/1992 |
| WO | WO 2008/015918 A1 | 2/2008 |
| WO | WO 2016/009202 A1 | 1/2016 |

OTHER PUBLICATIONS

Extended European Search Report for European Application No. 20788246.5, dated Dec. 7, 2022.
Chinese Office Action and Search Report for Chinese Application No. 202080027651.3, dated Dec. 14, 2022, with English translation.

* cited by examiner

AEROSOL SUPPLY DEVICE

CROSS REFERENCE TO RELATED APPLICATIONS

This application is a Continuation of PCT International Application No. PCT/JP2020/014316, filed on Mar. 27, 2020, which claims priority under 35 U.S.C. 119(a) to Patent Application No. 2019-074362, filed in Japan on Apr. 9, 2019, all of which are hereby expressly incorporated by reference into the present application.

TECHNICAL FIELD

The present invention relates to an aerosol supply device and relates to an aerosol supply device that supplies an aerosol to the outside.

BACKGROUND ART

In recent years, an aerosol supply device such as a flavor inhaler capable of providing a flavor without burning a flavor source such as tobacco has been in common use.

As another type of aerosol supply device, there has been known an inhaler capable of supplying a user with a liquid atomized by using ultrasonic waves.

For example, PTL 1 discloses a smoking device that atomizes a liquid aerosol-forming substrate, which has been supplied to an atomization region from a cartridge, by the vibration of a surface acoustic wave (SAW) generated by a transducer.

CITATION LIST

Patent Literature

PTL 1: U.S. Patent Application Publication No. 2017/0280771

SUMMARY OF INVENTION

Technical Problem

However, regarding the smoking device (aerosol supply device) in PTL 1, the liquid aerosol-forming substrate (liquid) is influenced by gravity according to the inclination of the aerosol supply device, and the amount of the liquid aerosol-forming substrate to be supplied to an atomization area to which the vibration is applied is thus changed, which may change the atomizing amount. Accordingly, there has been room for improvement in stabilizing the amount of liquid to be supplied to the atomization area to which the vibration is applied and in stabilizing the atomizing amount, regardless of the inclination of the aerosol supply device.

The present invention has been made in view of such problem described above, and an object thereof is to provide an aerosol supply device with which an atomizing amount can be stabilized regardless of the inclination thereof.

Solution to Problem

An aerosol supply device according to the present invention includes an accommodating section that accommodates a liquid, an atomizing unit that atomizes the liquid to generate an aerosol, and an atomizing amount adjusting unit that adjusts the atomizing amount of the atomizing unit. The aerosol supply device is characterized in that the atomizing amount adjusting unit stabilizes the atomizing amount regardless of the inclination of the aerosol supply device within at least a certain range.

Advantageous Effects of Invention

According to the aerosol supply device of the present invention, it is possible to stabilize the atomizing amount regardless of the inclination thereof.

DESCRIPTION OF EMBODIMENTS

Hereinafter, the embodiments according to the present invention will be described with reference to the drawings. Note that the embodiments described below are merely examples for facilitating understanding of the present invention, and the present invention is not limited thereto. That is, it goes without saying that, for example, the shapes, dimensions, and arrangement of the members described below can be modified and improved without departing from the spirit of the present invention and that the equivalents thereof are included in the present invention.

In addition, in all the drawings, constituents similar to one another are given similar references, and overlapping description will appropriately be omitted.

Outline

Figure 1:
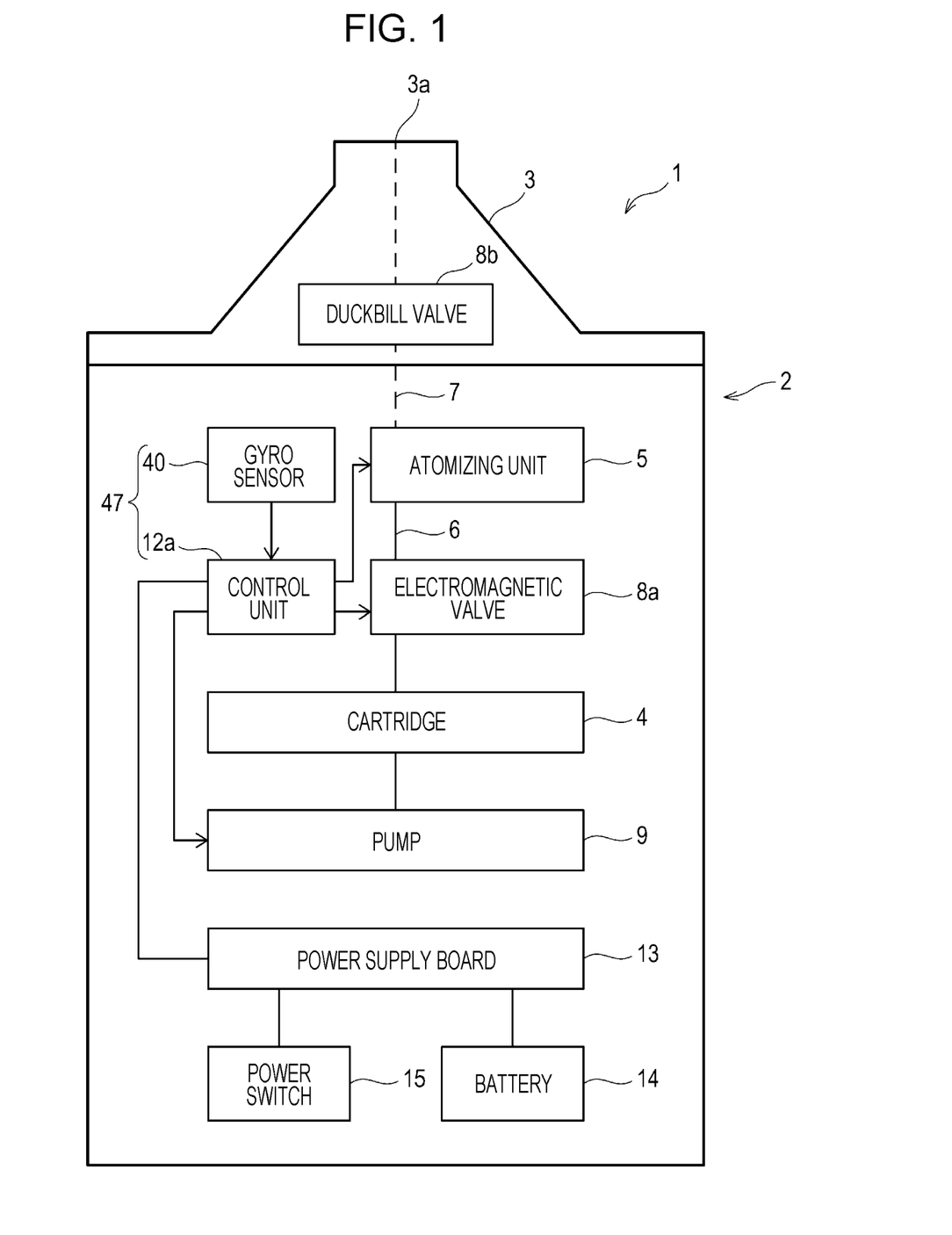
FIG. 1 schematically illustrates the configuration of an aerosol supply device according to a first embodiment.
Figure 2:
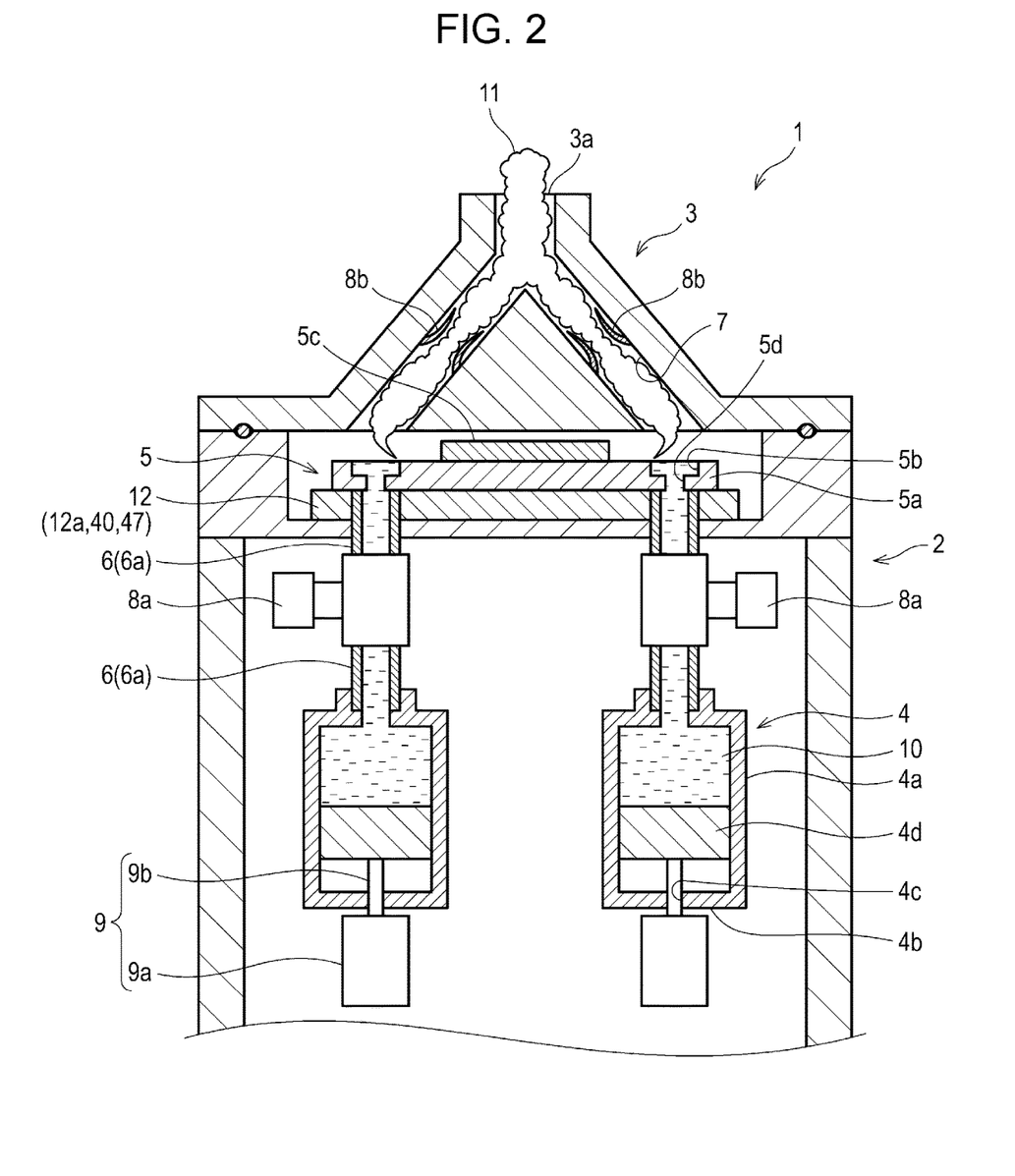
FIG. 2 is a schematic view illustrating the state where a liquid is atomized and discharged to outside the aerosol supply device.

First, the outline of an aerosol supply device 1 according to the present embodiment will be described with reference to FIGS. 1 and 2. FIG. 1 schematically illustrates the configuration of the aerosol supply device 1 according to a first embodiment. FIG. 2 is a schematic view illustrating the state where a liquid 10 is atomized and discharged to outside the aerosol supply device 1. Note that a gasket or a packing material is provided between corresponding ones of the members constituting the aerosol supply device 1 in view of sealing performance; however, for facilitating understanding, the illustration thereof is partially omitted in FIG. 2 and in FIGS. 4, 5, and 6 and other figures, which will be referred to later.

In addition, in FIG. 2 and in FIGS. 4 and 5 and other figures according to a second embodiment, which will be described later, the illustration of a power supply board 13 and a battery 14, which will be described later, is omitted. However, any arrangement thereof is possible. For example, the power supply board 13 and the battery 14 may be disposed below a cartridge 4 or may be disposed, relative to the cartridge 4, on the back side of the plane of each figure.

The aerosol supply device 1 according to the present embodiment is provided with: an accommodating section (cartridge 4) that accommodates the liquid 10; an atomizing unit 5 that atomizes the liquid 10 to generate an aerosol 11; and an atomizing amount adjusting unit 47 (gyro sensor 40 and control unit 12a) that adjusts the atomizing amount of the atomizing unit 5.

The atomizing amount adjusting unit 47 (gyro sensor 40 and control unit 12a) is characterized by stabilizing the atomizing amount regardless of the inclination of the aerosol supply device 1 within at least a certain range.

With the above-described configuration, since the aerosol supply device 1 includes the atomizing amount adjusting unit 47 (gyro sensor 40 and control unit 12a), it is possible to stabilize the atomizing amount regardless of the inclination of the aerosol supply device 1.

Here, the "atomizing amount adjusting unit" includes an "electric power adjusting portion" that adjusts the electric power to be supplied to, for example, the atomizing unit 5 (electrode 5c) or pumps 9, as described later, and includes an "inclination adjusting portion" that adjusts the inclination of a built-in unit 41, which will be described later, including the atomizing unit 5 so that retaining portions 5b, which will be described later, that retain the liquid 10 are in a horizontal state.

Moreover, the "atomizing amount adjusting unit" may also include, as a portion for adjusting the atomizing amount in response to the application of vibration, a "vibration adjusting portion" that suppresses or permits the vibration by changing the position at which the "vibration adjusting portion" is in physical contact with a vibratory element (piezoelectric element substrate 5a) or by separating from the vibratory element (piezoelectric element substrate 5a).

Furthermore, the "electric power adjusting portion" includes an "amplitude adjusting portion" that, according to the inclination of the aerosol supply device 1, adjusts the amplitude of the vibration (vibrational energy) of the vibratory element (piezoelectric element substrate 5a) by adjusting the electric power to be supplied to the electrode 5c, which will be described later. The "electric power adjusting portion" also includes a "liquid amount adjusting portion" that adjusts the amount of the liquid 10 to be supplied to the atomizing unit 5 by adjusting the electric power to be supplied to, for example, the pumps 9, which will be described later. Other than the above-described portions, the "electric power adjusting portion" includes a "temperature adjusting portion" that adjusts the temperature of an atomization region by adjusting the electric power to be supplied to a heater, which is not illustrated.

Such "stabilization of the atomizing amount" means that, specifically, the state where the atomizing amount is adjusted becomes nearer to a reference state than the state where the atomizing amount is not adjusted, when the reference state is the state where the surface of the liquid 10 retained in each of the retaining portions 5b, which will be described later, is positioned on the horizontal plane, that is, the state where the liquid 10 is retained while not leaning to one side and the vibrational energy of the piezoelectric element substrate 5a can be widely propagated.

First Embodiment

Configuration of Each Part

Figure 3:
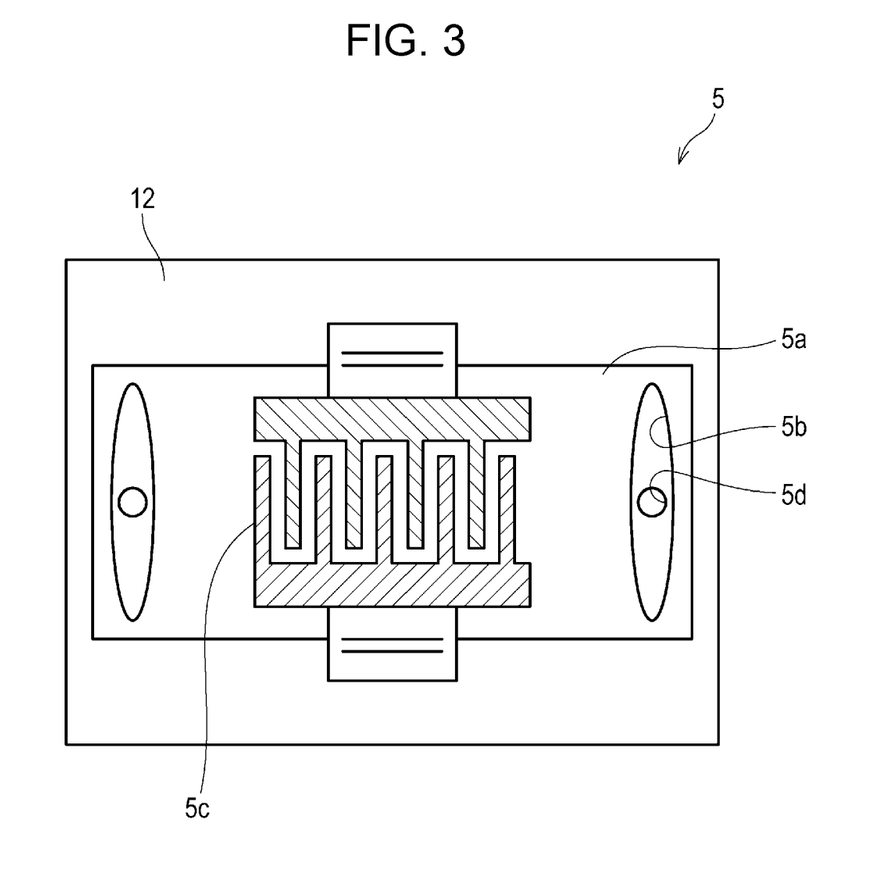
FIG. 3 is a plan view illustrating an atomizing unit.

Next, the configuration of each part of the aerosol supply device 1 will be described with reference to FIG. 3 in addition to FIGS. 1 and 2. FIG. 3 is a plan view illustrating the atomizing unit 5.

Atomizing Unit

As FIGS. 2 and 3 illustrate, the atomizing unit 5 is provided with a substrate (piezoelectric element substrate 5a) having the retaining portions 5b that retain the liquid 10 and having a piezoelectric body, and the electrode 5c that is disposed in contact with the piezoelectric element substrate 5a and supplies surface acoustic waves to the liquid 10 retained by the retaining portions 5b on the piezoelectric element substrate 5a.

Piezoelectric Element Substrate

Each of the retaining portions 5b provided in the piezoelectric element substrate 5a according to the present embodiment is formed in an upper surface of the piezoelectric element substrate 5a and is a bottomed groove formed to have an oval shape, in plan view, as FIG. 3 illustrates. The retaining portions 5b are disposed at least at two places, and the electrode 5c is disposed between the two places. A through hole 5d is formed in a center portion of each of the retaining portions 5b while passing through the piezoelectric element substrate 5a in the thickness direction thereof. The retaining portion 5b is supplied with the liquid 10 by the pump 9, which will be described later, from the cartridge 4 through a first flow passage 6 (tube 6a) and the through hole 5d.

Electrode

The electrode 5c is constituted by a comb-shaped electrode (interdigital transducer, also referred to as an IDT). The high frequency power input into the electrode 5c from the power supply board 13 via a control board 12 is converted into a surface acoustic wave (also referred to as a SAW) due to the piezoelectric phenomenon of the piezoelectric element substrate 5a and the surface acoustic wave is then propagated along a surface of the piezoelectric element substrate 5a and to both the sides thereof in the direction where the comb teeth are aligned.

The number of the comb teeth of the electrode 5c is not limited to that of the illustrated comb teeth and is determined based on the efficiency in atomizing the aerosol 11 by the surface acoustic wave. In addition, the width of each comb tooth and a gap between corresponding ones of the comb teeth are determined based on the frequency based on the particle size of the aerosol 11 to be atomized.

Regarding a surface acoustic wave, the control of, for example, the frequency of the electric power is important. Thus, there may be provided a resonance frequency monitoring sensor that monitors a resonance frequency or a temperature sensor, which is not illustrated, that can detect the temperature of the liquid 10 immediately before being atomized.

The aerosol supply device 1 according to the present embodiment is, regarding the appearance thereof, mainly constituted by a device main body 2 and a mouthpiece 3 that is attached to an upper portion of the device main body 2 and through which the aerosol 11 is discharged.

Mouthpiece

In front view, the mouthpiece 3 according to the present embodiment has a lower edge-side end portion extending widely and has a tapered portion in which the width thereof decreases as the portion extends toward a discharge port 3a that is disposed at the upper end and through which the aerosol 11 is discharged to the outside.

As FIG. 2 illustrates, the mouthpiece 3 has flow passages (second flow passages 7) through which the aerosol 11 generated from the atomizing unit 5 passes. Two flow passages (second flow passages 7) are separately disposed so as to cause the aerosol 11, which is generated from the liquid 10 in the retaining portions 5b at least at two places, to pass and are symmetrically formed about a virtual plane passing through the discharge port 3a. The two second flow passages 7 merge with one another to be one flow passage before reaching the discharge port 3a at the upper end.

In addition, the flow passages (second flow passages 7) disposed separately may be formed to have different lengths. That is, the two second flow passages 7 are not limited to the flow passages formed symmetrically about the virtual plane passing through the discharge port 3a and may alternatively have an asymmetrical shape. For example, when aerosols 11 that are different in components pass the two respective second flow passages 7, the lengths and shapes of the flow passages may be determined according to the aerosols 11.

In particular, for example, the two second flow passages 7, include an asymmetric portion. The asymmetric portion is formed, for example, by a curvature of one of the two second passages 7 that is different from that of the other one of the two second passages 7.

With the above-described configuration, it is possible to deposit and reduce the particles contained in the aerosols to adjust the particle size of the particles when the aerosols 11 come into contact with the wall surfaces defining the asymmetric portion that have different bending rate and that is the portion in relation to the two second flow passages 7. Thus, a user can smoothly inhale the aerosol 11 without the component of the aerosol 11 causing the throat to feel uncomfortable.

Note that the concept of "bending" is not limited to bending sharply and includes bending gently. The two second flow passages 7 having different bending rates are not limited to the flow passages each formed to be bent, and the instance where one of the flow passages is formed straight is also included.

Device Main Body

Inside the device main body 2 according to the present embodiment, there are provided the cartridges 4, the above-described atomizing unit 5, electromagnetic valves 8a, the pumps 9, the control board 12 including the control unit 12a, the power supply board 13 and the battery 14 that are illustrated in FIG. 1, and a portion of a power switch 15.

In addition, in the device main body 2, the flow passages (first flow passages 5) for the liquid 10 are formed between the accommodating section (cartridge 4), which will be described later, and the atomizing unit 5. Moreover, between the atomizing unit 5 and the outside, the flow passages (second flow passages 7) for the aerosol 11 are formed in a region from the device main body 2 to the mouthpiece 3.

Cartridge

Each of the cartridges 4 according to the present embodiment is constituted by a main body 4a, a bottom plate 4b formed integrally with a bottom portion of the main body 4a, and a sliding block 4d disposed inside the main body 4a, water-tightly disposed on the inner wall surface of the main body 4a, and being able to slide inside the main body 4a.

The bottom plate 4b has a through hole 4c passing through the bottom plate 4b in the thickness direction, and a pushing rod 9b of the pump 9, which will be described later, is configured to be insertable into the through hole 4c.

The present embodiment has a configuration in which liquids 10 are separately supplied from the respective two cartridges 4 to the respective two retaining portions 5b disposed in the piezoelectric element substrate 5a of the atomizing unit 5.

However, the present invention is not limited to such a configuration and may have a configuration in which the liquid 10 is supplied from the single cartridge 4 to the two retaining portions 5b. With such a configuration, the number of the electromagnetic valves 8a, which will be described later, can be reduced. That is, an electromagnetic valve 8a may be disposed at a tube 6a, on the cartridge 4 side, that does not start branching toward the two retaining portions 5b.

With such a configuration, it is possible to adjust the supply of the liquid 10 to the two retaining portions 5b and the stop of the supply of the liquid 10 by using the single electromagnetic valve 8a.

Note that the aerosol supply device 1 may further be provided with plural cartridges 4. In addition, when two or more cartridges 4 are used, liquids 10 that contain different taste or flavor components, for example, may be accommodated in the respective cartridges 4.

Note that the accommodating section according to the present invention is not limited to the detachable cartridge 4 and may be a container that is fixed to the device main body 2 (that is, a refillable type). Even when the fixed container is used as described above, another flow passage leading to the container and the outside is formed, and the container may be filled with the liquid 10 by the liquid 10 being injected into the container through this flow passage.

With such a configuration, when the container is refilled with the liquid 10, a user does not need to detach and reattach the installed electromagnetic valve 8a, cartridge 4, and the tube 6a connecting the electromagnetic valve 8a to the cartridge 4.

Liquid

The liquid 10 may contain solvents such as water, glycerin, propylene glycol, and ethanol and may also contain a solute containing, for example, a taste or flavor component. Examples of such a solute are volatile components such as a tobacco extract, menthol, linalool, limonene, and vanillin, or nonvolatile components such as saccharides including fructose, glucose, sucrose, and lactose, acids including malic acid and citric acid, or salts.

The liquid 10 may be in a state of being emulsified by an emulsifier or in a state of being suspended by a dispersant.

Inside the device main body 2, the electromagnetic valve 8a is connected between the tubes 6a connecting the cartridge 4 to the atomizing unit 5.

The electromagnetic valve 8a is provided with an opening and closing portion, which is not illustrated, that operates so as to be able to open and close the flow passage (first flow passage 6) for the liquid 10.

With the above-described configuration, the control unit 12a causes the opening and closing portion of the electromagnetic valve 8a to operate to block the first flow passage 6, and it is thereby possible to prevent the liquid 10 from volatilizing from the accommodating section (cartridge 4). In addition, the control unit 12a causes the opening and closing portion of the electromagnetic valve 8a to operate to open the first flow passage 6, and it is thereby possible to supply the liquid 10 to the atomizing unit 5 and further possible to supply the aerosol 11 to a user.

Each duckbill valve 8b according to the present embodiment is a valve constituted by mutually facing flat plates made of a soft resin material, and the facing interval between the flat plates decreases as the flat plates extend toward the downstream (inhalation) side. The duckbill valve 8b, in a natural state, blocks the flow passage by the flat plates being in contact with one another and opens the flow passage by the flat plates separating from one another due to the inhalation pressure from the downstream side.

Since the duckbill valve 8b functions as a small check valve to allow the flow passage for the aerosol 11 to narrow, the size of the mouthpiece 3 can thereby be reduced, and, furthermore, the size of the aerosol supply device 1 can be reduced. In addition, the duckbill valve 8b is preferable because the duckbill valve 8b can be opened by a weak inhalation force without being affected in the gravitational direction, and, due to an elastic resilient force, the opening and closing portion can close by itself when the inhalation is stopped. The duckbill valve 8b is disposed between the retaining portion 5b and the discharge port 3a.

Pump

The aerosol supply device 1 is further provided with the pumps 9 capable of supplying the liquid 10 to the atomizing unit 5. Each of the pumps 9 according to the present embodiment is a syringe pump capable of pulling the liquid 10 from the atomizing unit 5 back to the accommodating section (cartridge 4) side.

Specifically, the pump 9 includes a motor 9a and the pushing rod 9b that can advance and retreat according to the rotating operation of the motor 9a. When the pushing rod 9b passes through the through hole 4c and pushes the sliding block 4d upward due to the pump 9 operating, the liquid 10 is pushed by the sliding block 4d to be supplied to the atomizing unit 5.

However, the pump according to the present invention is not limited to a pump having such a configuration and may be, for example, a piezoelectric pump, which is not illustrated. With such a piezoelectric pump, it is possible to provide a low power consuming product.

Atomizing Amount Adjusting Unit

The atomizing amount adjusting unit 47 includes an inclination detection sensor (gyro sensor 40) that detects the inclination of the aerosol supply device 1, and the control unit 12a that adjusts, in response to a signal received from the inclination detection sensor, the electric power for atomization to be supplied to the atomizing unit 5.

With the above-described configuration, the electric power to be supplied to the atomizing unit 5 (electrode 5c) is adjusted according to the inclination, and, due to such an increase and decrease in the electric power, the amplitude of the vibration is adjusted. Thus, the atomizing amount can be stabilized in a state where the atomizing amount is not much changed from the atomizing amount when the aerosol supply device 1 is in the normal inclination thereof.

That is, the atomizing amount adjusting unit 47 is the electric power adjusting portion that adjusts the electric power to be supplied to the electrode 5c, which is related to the amplitude of the piezoelectric element substrate 5a, and is also the amplitude adjusting portion that adjusts the amplitude (vibrational energy) of the piezoelectric element substrate 5a, according to the inclination of the aerosol supply device 1.

Inclination Detection Sensor

The gyro sensor 40 is a sensor that detects the inclination (slant) of the aerosol supply device 1 (atomizing unit 5) and is mounted on the control board 12. The gyro sensor 40 according to the present embodiment is a "vibration type". The gyro sensor 40 is provided with a vibrator, which is not illustrated, disposed on a silicon substrate, which is not illustrated, and an electrode, which is not illustrated, disposed in the vicinity of the vibrator inside the gyro sensor 40. The gyro sensor 40 is a sensor that detects a swing (slant) by detecting an electrical difference according to a change in an electrostatic capacitance caused by a Coriolis force generated between the vibrator and the electrode when the vibrator is vibrated.

Note that the gyro sensor 40 is not limited to an electrostatic capacity type, may be a piezoelectric type, and may further be, other than the vibration type, for example, an optical type.

In addition, the inclination detection sensor is not limited to the gyro sensor 40 and may be, for example, a liquid amount sensor, which is not illustrated, constituted by plural electrodes.

For example, the liquid amount sensor is configured so that a portion of the electrodes comes into contact with the liquid 10 when the aerosol supply device 1 is inclined. When paired electrodes are energized by coming into contact with the liquid 10, the control unit 12a that has received the electrical signal from the paired electrodes determines that the liquid 10 is at the position of the paired electrodes, thereby determining the inclination of the aerosol supply device 1 according to the position of the liquid 10.

Control Board

The aerosol supply device 1 is provided with the control board 12 having the control unit 12a that controls various electronic devices such as the pump 9, the electromagnetic valve 8a, and an electric power adjusting device, which is not illustrated.

When the aerosol supply device 1 is brought into operation by a user operating the power switch 15, and the control unit 12a receives a signal transmitted from the power supply board 13, the control unit 12a according to the present embodiment brings the electromagnetic valve 8a that is in a closed state, which is a normal state, into an open state.

Under the control of the control unit 12a, the atomizing unit 5 supplies electric power to the electrode 5c to generate surface acoustic waves on the surface of the piezoelectric element substrate 5a.

Moreover, the control unit 12a causes the motor 9a of the pump 9 to operate so that the pushing rod 9b pushes the sliding block 4d in the direction (upward) in which the volumetric capacity of the cartridge 4 is reduced. Thus, the liquid 10 is supplied to the retaining portion 5b through the first flow passage 6 and resonates with the surface acoustic waves to be atomized at the surface of the piezoelectric element substrate 5a.

In such a state, a user inhales the air inside the aerosol supply device 1 through the discharge port 3a, and the pressure of a region of the duckbill valve 8b on the discharge port 3a side thereby becomes negative. Thus, the duckbill valve 8b is opened, and the user can inhale the aerosol 11 that has passed through the duckbill valve 8b.

In addition, the control unit 12a causes the electromagnetic valve 8a to operate to close the flow passage for the liquid 10, when the aerosol supply device 1 is brought into a non-use state, that is, for example, when the power switch 15 is switched off.

In addition, the control unit 12a determines whether the aerosol supply device 1 (piezoelectric element substrate 5a) is inclined, according to a signal from the gyro sensor 40 mounted on the control board 12. When determining that the aerosol supply device 1 is inclined, the control unit 12a performs control so that the electric power to be supplied to the atomizing unit 5 (electrode 5c) becomes larger than the electric power supplied when the aerosol supply device 1 is in the normal inclination.

In this way, the aerosol supply device 1 according to the present embodiment is capable of stabilizing the atomizing amount of the liquid 10 even when the amount of the liquid 10 to which the vibration of the piezoelectric element substrate 5a is propagated becomes small due to the inclination of the piezoelectric element substrate 5a. Specifically, the aerosol supply device 1 is capable of stabilizing the atomizing amount of the liquid 10 by increasing the vibrational energy to be propagated to the liquid 10 by the control unit 12a controlling the atomizing unit 5 (electrode 5c).

In addition, the atomizing amount adjusting unit 47 may include the control unit 12a that adjusts the amount of the liquid 10 to be supplied to the atomizing unit 5 in response to a signal received from the inclination detection sensor (gyro sensor 40).

With the above-described configuration, it is possible to stabilize the atomizing amount by adjusting, according to the inclination, the amount of the liquid 10 to be supplied to the atomizing unit 5.

That is, the atomizing amount adjusting unit 47 is the electric power adjusting portion that adjusts the electric power to be supplied to, for example, the pump 9 according to the inclination of the aerosol supply device 1 and is also the liquid amount adjusting portion that adjusts the amount of the liquid 10 to be supplied to the atomizing unit 5.

For example, when determining that the aerosol supply device 1 (piezoelectric element substrate 5a) is inclined according to the signal from the gyro sensor 40 mounted on the control board 12, the control unit 12a controls the pump 9 so that the amount of the liquid 10 to be supplied to the atomizing unit 5 (retaining portion 5b) becomes larger than the amount of the liquid 10 supplied when the aerosol supply device 1 is in the normal inclination.

In this way, when the piezoelectric element substrate 5a is inclined, and the amount of the liquid 10 to which the vibration of the piezoelectric element substrate 5a is propagated becomes small, it is possible to increase the amount of the liquid 10 to be supplied to the atomizing unit 5 by the control unit 12a controlling the pump 9. Accordingly, the atomizing amount of the liquid 10 becomes stabilized.

The control target of the control unit 12a for the purpose of adjusting the amount of the liquid 10 to be supplied as described above is not limited to the pump 9 and may be, for example, the electromagnetic valve 8a or another electronic device that narrows and widens the flow passage.

Note that the above-described atomizing amount adjusting unit 47 may separately or simultaneously adjust the electric power and the amount of the liquid 10 that are supplied to the atomizing unit 5, according to the atomizing amount.

For example, the aerosol supply device 1 may be provided with a heater, which is not illustrated, for heating the liquid 10 to increase the atomizing amount, and the atomizing amount may be adjusted by adjusting the electric power to be supplied to the heater.

Second Embodiment

Next, an aerosol supply device 1A according to the second embodiment will be described with reference mainly to FIGS. 4 and 5. FIG. 4 is a schematic view illustrating the aerosol supply device 1A according to the second embodiment. FIG. 5 is a schematic view illustrating the state where the aerosol supply device 1A in the state illustrated in FIG. 4 is inclined 90 degrees.

Figure 4:
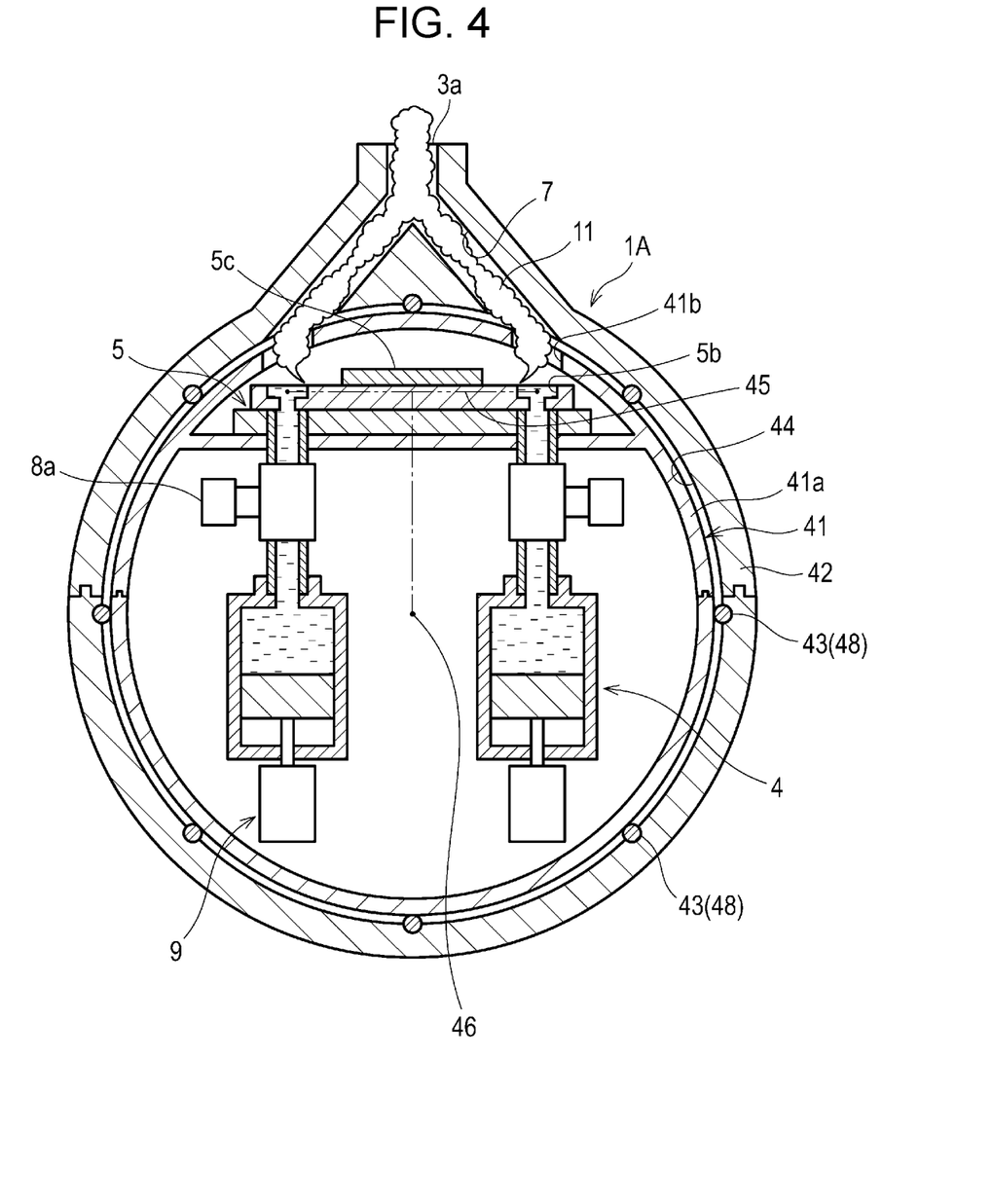
FIG. 4 is a schematic view illustrating an aerosol supply device according to a second embodiment.

Note that, regarding the aerosol supply device 1A, FIG. 4 illustrates the configuration without a duckbill valve 8b on each second flow passage 7; however, a duckbill valve 8b may be provided as with the configuration of the first embodiment.

The aerosol supply device 1A according to the present embodiment is further provided with the built-in unit 41 including at least the atomizing unit 5 and a housing 42 covering the built-in unit 41.

An atomizing amount adjusting unit 48 has an inclination maintaining portion (ball transfer 43) that maintains the inclination of the built-in unit 41 regardless of the inclination of the aerosol supply device 1A within at least a certain range.

The atomizing amount adjusting unit 48 functions as an "inclination adjusting portion" that adjusts the inclination of the built-in unit 41 including the atomizing unit 5 so that the retaining portions 5b that retain the liquid 10 are in a horizontal state.

The expression "regardless of the inclination of the aerosol supply device 1A" means, regarding the present embodiment, a state of being irrelevant to the relative inclinations of the housing 42 and the built-in unit 41. In addition, "maintaining the inclination of the built-in unit 41 regardless of the inclination of the aerosol supply device 1A" also includes a state of maintaining the inclination of the built-in unit 41 only when the housing 42 is inclined within a certain range.

With the above-described configuration, the built-in unit 41 including the atomizing unit 5 is configured to maintain the inclination thereof due to the ball transfers 43 regardless of the inclination of the aerosol supply device 1A, and it is thereby possible to stabilize the atomizing amount.

The built-in unit 41 is provided with the atomizing unit 5, the electromagnetic valves 8a, the pumps 9, the control board 12, the power supply board 13, and the battery 14, which are described while illustrated in FIGS. 1 and 2, and a spherical (substantially spherical) case 41a covering these parts. Note that, the shape of the case 41a may be any shape having a spherical outer surface that is connected to the housing 42, which will be described later, with the ball transfers 43 therebetween, and the shape of the inner surface, which may have any appropriate shape, may have, for example, a rectangular parallelepiped shape. In addition, the shape of the outer surface of the case 41*a* is not limited to a perfectly spherical shape, and at least a portion of the outer surface of the case 41*a* facing the housing 42 may be formed to have a spherical shape.

An upper portion of the case 41*a* has passing holes 41*b* that pass through the case 41*a* in the vertical direction and are formed at the same interval as that of the two retaining portions 5*b* disposed in the piezoelectric element substrate 5*a*. Each of the passing holes 41*b* has a function of causing the aerosol 11 generated from the atomizing unit 5 to pass through second flow passage 7 via a space 44, which will be described later.

The housing 42 has a drop shape and is formed slightly larger than the built-in unit 41, and the built-in unit 41 is built therein. Note that, the shape of the housing 42 may be any shape having a spherical inner surface that is connected to the case 41*a* with the ball transfers 43 therebetween and the shape of the outer surface, which may have any appropriate shape, may have, for example, a rectangular parallelepiped shape. In addition, the shape of the inner surface of the housing 42 is not limited to a perfectly spherical shape, and at least a portion of the inner surface of the housing 42 facing the case 41*a* may be formed spherical.

The ball transfers 43 are embedded in the inner surface of the housing 42. The built-in unit 41 is supported by the ball transfers 43 of the housing 42 so as to be able to relatively rotate in any direction.

The built-in unit 41 according to the present embodiment is configured to be rotatable 360 degrees even when, with respect to the housing 42, the built-in unit 41 is rotated about a direction of any one of the axes: the roll axis, the pitch axis, and the yaw axis.

Figure 5:
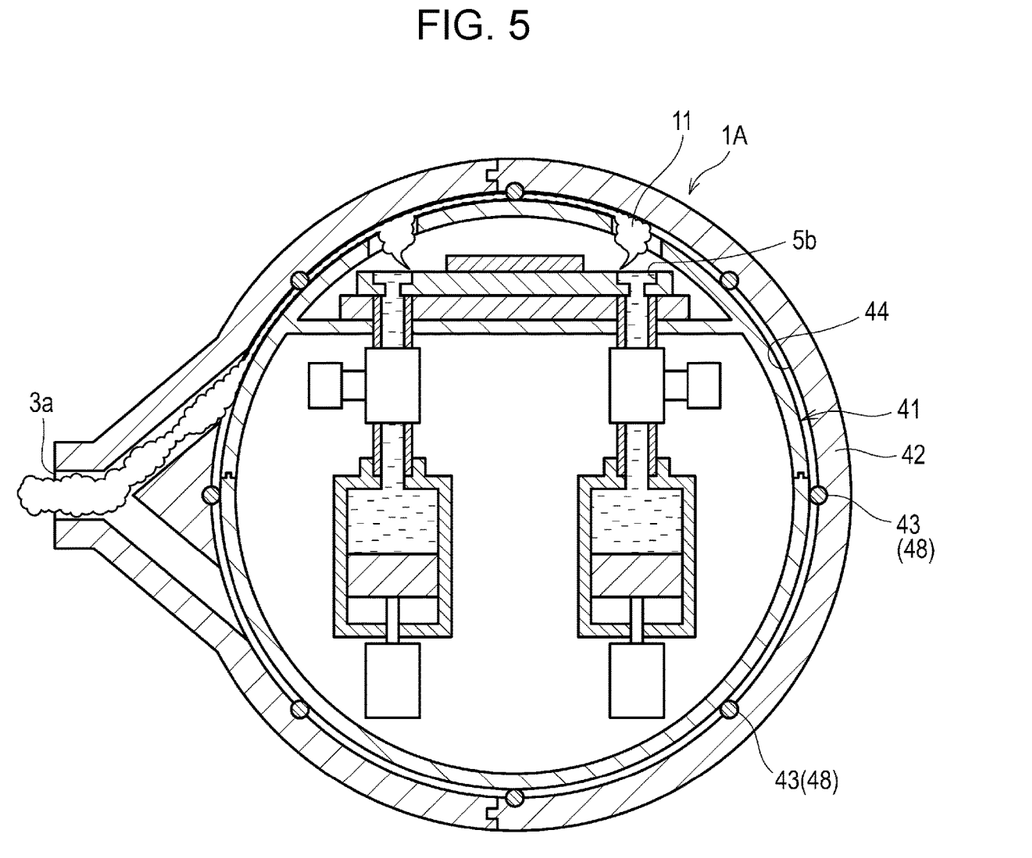
FIG. 5 is a schematic view illustrating the state where the aerosol supply device in the state illustrated in FIG. 4 is inclined 90 degrees.

As FIG. 5 illustrates, even when the housing 42 is inclined, the aerosol 11 can pass the space 44 to be discharged through the discharge port 3*a* by a user inhaling the air inside the aerosol supply device 1A through the discharge port 3*a* to apply negative pressure.

The configuration of the aerosol supply device 1A according to the present embodiment is partially the same as that of the aerosol supply device 1 according to the above-described embodiment. Specifically, the aerosol supply device 1A is an aerosol supply device 1A that atomizes the liquid 10, by vibration, to supply the aerosol 11. The atomizing unit 5 is provided with the retaining portions 5*b* that retain the liquid 10, a vibratory element (piezoelectric element substrate 5*a*) that forms the aerosol 11 by vibrating the liquid 10 retained in the retaining portions 5*b*, and the comb-shaped electrode 5*c* (vibration source to vibrate the vibratory element) that generates surface acoustic waves at the surface of the piezoelectric element substrate 5*a* by being supplied with electric power. The retaining portions 5*b* are paired and disposed with the piezoelectric element substrate 5*a* therebetween.

The built-in unit 41 has a center of gravity 46 at a position below the midpoint of a virtual line segment 45 connecting the center points of the respective paired retaining portions 5*b*, that is, below the retaining portions 5*b* and in the direction normal to the surface of the piezoelectric element substrate 5*a*.

Note that, to make the load distribution in a region of the center of gravity 46 denser, a weight portion, which is not illustrated, may further be provided below the midpoint of the virtual line segment 45 connecting the center points of the respective paired retaining portions 5*b* (in the present embodiment, between the paired motors 9*a*). Such a weight portion may be any weight portion having a function of stabilizing the weight balance, and the weight portion may optionally have other functions.

With such a configuration, the center of gravity 46 can surely be positioned below the midpoint of the virtual line segment 45 connecting the center points of the respective paired retaining portions 5*b*. In addition, with the configuration, with respect to a change of the inclination of the aerosol supply device 1A, the responsiveness of the inclination correction of the built-in unit 41 can be increased due to the weight of the built-in unit 41 including the weight portion, which is not illustrated.

With the above-described configuration, regarding the built-in unit 41, the paired retaining portions 5*b* can be held on the horizontal plane due to the center of gravity of the built-in unit 41; thus, even when the paired retaining portions 5*b* are provided, it is possible to stabilize the atomizing amount of the liquid 10 to be atomized from the paired retaining portions 5*b*.

For example, as FIG. 5 illustrates, only the housing 42 is inclined when the aerosol supply device 1A in the state illustrated in FIG. 4 is inclined 90 degrees. At this time, the built-in unit 41 is caused to maintain the inclination by the center of gravity thereof, and only the housing 42 is inclined by the ball transfers 43 of the housing 42 rotating so as to roll while being in contact with the outer surface of the built-in unit 41.

That is, the ball transfers 43, by rolling, maintain the built-in unit 41 in the inclination in which the retaining portions 5*b* are horizontally disposed, regardless of the inclination of the aerosol supply device 1A. Thus, the ball transfers 43 hold the retaining portions 5*b* in a horizontal state, thereby functioning as the atomizing amount adjusting unit 48 (inclination adjusting portion) that stabilizes the atomizing amount.

In the above-described configuration, the atomizing unit 5 is described as an atomizing unit provided with a pair of the pumps 9 and a pair of the retaining portions 5*b*; however, the atomizing unit 5 according to the present invention is not limited to such a configuration. For example, a single pump 9 and a single retaining portion 5*b* may be provided.

In this instance, the built-in unit 41 may have the center of gravity at a position below the retaining portion 5*b* and in the direction normal to the surface of the piezoelectric element substrate 5*a*.

With such a configuration, the retaining portion 5*b* can be held on the horizontal plane due to the center of gravity of the built-in unit 41, and it is thereby possible to stabilize the atomizing amount of the liquid 10.

Each of the ball transfers 43 may be provided with, in addition to the illustrated large ball, a small ball that rolls while being in contact with the large ball and is smaller than the large ball. Such a configuration is preferable because the rolling performance of the large ball is increased, and the necessity of a lubricant for maintaining the rolling performance of the large ball is reduced. In this instance, the small ball may be accommodated in a portion of a hole in which the large ball is held.

In addition, in the above-described embodiment, the ball transfers 43 maintain the inclination of the built-in unit 41; however, the present invention is not limited to such a configuration. For example, a liquid such as water may be accommodated in a portion of a region between the built-in unit 41 and the housing 42, and the built-in unit 41 may float on the liquid. In this instance, it is preferable that the buoyancy of the built-in unit 41 be increased by the built-in unit 41 including, for example, an air bladder or a styrene foam portion that has a density lower than that of the liquid.

Note that the built-in unit 41 according to the present embodiment is configured to be rotatable 360 degrees even when, with respect to the housing 42, the built-in unit 41 is rotated about any one of the axes: the roll axis, the pitch axis, and the yaw axis; however, the built-in unit 41 according to the present embodiment is not limited to such a configuration. For example, the built-in unit 41 may be rotatable only at some angles, for example, only in an angle range of 180 degrees in one direction, that is, only in the hemispherical range in three dimensions.

In this instance, for example, when the built-in unit 41 is inclined beyond the rotatable range, that is, when the retaining portions 5b are not positioned on the horizontal plane, the control unit 12a may perform another control, which is described above, for stabilizing the atomizing amount (controlling the electric power to be supplied or controlling the amount of the liquid 10 to be supplied).

Third Embodiment

Figure 6:
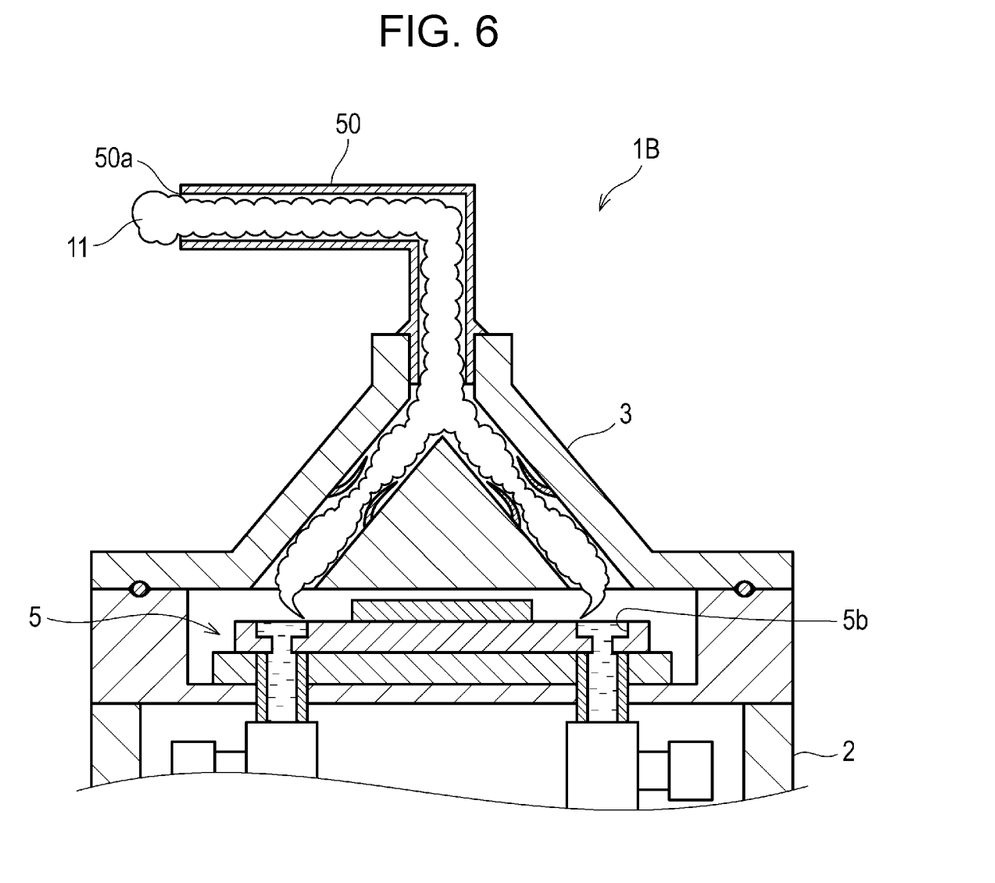
FIG. 6 is a schematic view illustrating the configuration of the vicinity of a discharge pipe of an aerosol supply device according to a third embodiment.

Lastly, an aerosol supply device 1B according to a third embodiment will be described with reference mainly to FIG. 6. FIG. 6 is a schematic view illustrating the configuration of the vicinity of a discharge pipe 50 of the aerosol supply device 1B according to the third embodiment.

The aerosol supply device 1B according to the present embodiment is further provided with a discharge portion (discharge pipe 50) having a discharge port 50a through which the aerosol 11 is discharged to the outside. In addition, as with the above-described embodiments, the atomizing unit 5 includes the retaining portions 5b that retain the liquid 10 to be atomized.

The discharge port 50a is directed in a direction intersecting the direction normal to an extension surface in which the retaining portions 5b extend.

Specifically, the discharge pipe 50 has a shape bent at a right angle (including a substantially right angle) and is vertically inserted into and fixed to the mouthpiece 3 by, for example, welding.

The position at which a user holds the discharge port 3a in the mouth is diagonal to the position at which the user grips the device main body 2 of the aerosol supply device 1B, unless the user sticks out the neck. Thus, if the discharge port 3a is directed in the direction normal to the extension surface of the retaining portions 5b, the atomizing unit 5 tends to be inclined.

Thus, as in the above-described configuration, the discharge port 50a is directed in the direction intersecting the direction normal to the extension surface in which the retaining portions 5b extend, and inhaling the aerosol 11 in the state where the retaining portions 5b (atomizing unit 5) are inclined is thereby easily avoided. That is, the retaining portions 5b are easily held in a horizontal state, and it is thereby possible to stabilize the atomizing amount of the liquid 10.

In addition, the discharge pipe 50 may extend on a horizontal plane including the retaining portions 5b, and a flow passage of the discharge pipe 50 and the discharge port 50a may be disposed on the horizontal plane.

The aerosol supply device 1B is further provided with a grip portion (the outer surface of the device main body 2) to be gripped by a user.

The discharge port 3a is disposed at a position apart from the grip portion (the outer surface of the device main body 2) in the direction normal to the extension surface in which the retaining portions 5b extend.

With the above-described configuration, by the discharge port 3a being disposed at a position apart from the grip portion (the outer surface of the device main body 2) in the direction normal to the extension surface in which the retaining portions 5b extend, the above-described direction normal to the extension surface (that is, the orientation of the device main body 2) is easily directed vertically in a natural manner.

Specifically, when the user grips the aerosol supply device 1B (device main body 2) and tries to inhale the aerosol 11 through the discharge port 3a, the device main body 2 is easily directed vertically, the retaining portions 5b are easily held horizontally, and the atomizing amount is easily stabilized.

Any configuration in which the discharge port 3a is directed in the direction intersecting the direction normal to the extension surface in which the retaining portions 5b extend is possible; thus, the discharge pipe 50 is not limited to a pipe having a shape bent at a right angle and may be curved in an arc shape.

To adjust the atomizing amount, the aerosol supply device 1 according to the above-described embodiment requires constituents (gyro sensor 40 and control unit 12a) for adjusting the electric power to be supplied to, for example, the atomizing unit 5 or the pump 9. In addition, the aerosol supply device 1A requires a constituent (ball transfer 43) that can adjust the inclination of the built-in unit 41 with respect to the housing 42.

In contrast, the aerosol supply device 1B according to the present embodiment does not require such constituents; thus, increase in the number of parts can be suppressed, and the price of a product can be reduced.

The aerosol supply device according to the present invention is not limited to an aerosol supply device that performs atomization by using a SAW and may be an aerosol supply device that performs atomization by using heating equipment such as a heater or by using an ultrasonic oscillator.

Moreover, the aerosol supply device may be, other than an electronic cigarette, a device such as an inhaler that spouts a solution or a diffuser that diffuses a flavor.

Furthermore, in the above-described embodiments, the configuration in which the liquid 10 is supplied from below toward the piezoelectric element substrate 5a is described as an example; however, the configuration is not limited to such a configuration, and the Liquid 10 may drip from above onto the piezoelectric element substrate 5a.

Note that the various constituents of the aerosol supply device according to the present invention are not necessarily be independent from one another. It is accepted that, for example, plural constituents are formed into one member, one constituent is formed of plural members, one constituent is part of another constituent, and a portion of one constituent and a portion of another constituent overlap with one another.

The present application claims priority based on Japanese Patent Application No. 2019-074362 filed on Apr. 9, 2019, the entire disclosure of which is incorporated herein by reference.

The above-described embodiments include the following technical concepts.

(1) An aerosol supply device including:
an accommodating section that accommodates a liquid;
an atomizing unit that atomizes the liquid to generate an aerosol; and
an atomizing amount adjusting unit that adjusts an atomizing amount of the atomizing unit, in which the atomizing amount adjusting unit stabilizes the atomizing amount regardless of an inclination of the aerosol supply device within at least a certain range.

(2) The aerosol supply device according to (1), in which the atomizing amount adjusting unit includes an inclination detection sensor that detects the inclination of the aerosol supply device and a control unit that adjusts, in response to a signal received from the inclination detection sensor, electric power for atomization to be supplied to the atomizing unit.

(3) The aerosol supply device according to (1) or (2), in which the atomizing amount adjusting unit includes an inclination detection sensor that detects the inclination of the aerosol supply device and a control unit that adjusts, in response to a signal received from the inclination detection sensor, an amount of the liquid to be supplied to the atomizing unit.

(4) The aerosol supply device according to any one of (1) to (3), further including:

a built-in unit including at least the atomizing unit; and a housing covering the built-in unit, in which the atomizing amount adjusting unit includes an inclination maintaining portion that maintains an inclination of the built-in unit regardless of the inclination of the aerosol supply device within at least a certain range.

(5) The aerosol supply device according to (4), in which the atomizing unit includes a retaining portion that retains the liquid, a vibratory element that forms the aerosol by vibrating the liquid retained in the retaining portion, and a vibration source that vibrates the vibratory element by receiving electric power, in which a center of gravity of the built-in unit is positioned below the retaining portion, and in which the inclination maintaining portion maintains an inclination of the built-in unit such that the retaining portion is disposed horizontally.

(6) The aerosol supply device according to any one of (1) to (3), further including:

a discharge portion having a discharge port through which the aerosol is discharged to an outside, in which the atomizing unit has a retaining portion that retains the liquid to be atomized, and in which the discharge port is directed in a direction intersecting a direction normal to an extension surface in which the retaining portion extends.

(7) The aerosol supply device according to (6), further including:

a grip portion to be gripped by a user, in which the discharge port is disposed at a position apart from the grip portion in the direction normal to the extension surface in which the retaining portion extends.

REFERENCE SIGNS LIST 1, 1A, 1B aerosol supply device
2 device main body (grip portion)
3 mouthpiece
3a discharge port
4 cartridge (accommodating section)
4a main body
4b bottom plate
4c through hole
4d sliding block
5 atomizing unit
5a piezoelectric element substrate (vibratory element)
5b retaining portion
5c electrode (vibration source)
5d through hole
6 first flow passage (flow passage for liquid)
6a tube
7 second flow passage (flow passage for aerosol)
8a electromagnetic valve
8b duckbill valve
9 pump
9a motor
9b pushing rod
10 liquid
11 aerosol
12 control board
12a control unit
13 power supply board
14 battery
15 power switch
40 gyro sensor (inclination detection sensor)
41 built-in unit
41a case
41b passing hole
42 housing
43 ball transfer (inclination maintaining portion, inclination adjusting portion)
44 space
45 virtual line segment
46 center of gravity
47 atomizing amount adjusting unit (electric power adjusting portion, amplitude adjusting portion, liquid amount adjusting portion)
48 atomizing amount adjusting unit (inclination adjusting portion)
50 discharge pipe (discharge portion)
50a discharge port

The invention claimed is:

1. An aerosol supply device comprising:
an accommodating section that accommodates a liquid;
an atomizer that atomizes the liquid to generate an aerosol;
an atomizing amount adjuster that adjusts an atomizing amount of the atomizer;
a built-in cartridge including at least the atomizer; and
a housing covering the built-in cartridge,
wherein the atomizing amount adjuster stabilizes an atomizing amount regardless of an inclination of the aerosol supply device within at least a certain range, and
wherein the atomizing amount adjuster includes an inclination maintaining portion that maintains an inclination of the built-in cartridge regardless of the inclination of the aerosol supply device within at least the certain range.

2. The aerosol supply device according to claim 1, wherein the atomizing amount adjuster includes an inclination detection sensor that detects the inclination of the aerosol supply device and a control unit that adjusts, in response to a signal received from the inclination detection sensor, electric power for atomization to be supplied to the atomizer.

3. The aerosol supply device according to claim 1, wherein the atomizing amount adjuster includes an inclination detection sensor that detects the inclination of the aerosol supply device and a control unit that adjusts, in response to a signal received from the inclination detection sensor, an amount of the liquid to be supplied to the atomizer.

4. The aerosol supply device according to claim 1, wherein the atomizer includes:

a retaining portion that retains the liquid, a vibratory element that forms the aerosol by vibrating the liquid retained in the retaining portion, and a vibration source that vibrates the vibratory element by receiving electric power, wherein a center of gravity of the built-in cartridge is positioned below the retaining portion, and wherein the inclination maintaining portion maintains the inclination of the built-in cartridge such that the retaining portion is disposed horizontally.

5. The aerosol supply device according to claim 1, further comprising:

a discharge portion having a discharge port through which the aerosol is discharged to an outside, wherein the atomizer has a retaining portion that retains the liquid to be atomized, and wherein the discharge port is directed in a direction intersecting a direction normal to an extension surface in which the retaining portion extends.

6. The aerosol supply device according to claim 5, further comprising:

a grip portion to be gripped by a user, wherein the discharge port is disposed at a position apart from the grip portion in the direction normal to the extension surface in which the retaining portion extends.

7. The aerosol supply device according to claim 1, wherein the atomizer includes retaining portions that retain the liquid, and wherein the inclination maintaining portion maintains the inclination of the built-in cartridge such that the retaining portions are disposed horizontally.

* * * * *